United States Patent [19]

Braun, Jr. et al.

[11] Patent Number: 4,963,138
[45] Date of Patent: Oct. 16, 1990

[54] NEO-NATAL NET

[76] Inventors: Nohl A. Braun, Jr.; Mary J. Urling, both of 1402 Mt. Vernon Rd., Charleston, W. Va. 25314

[21] Appl. No.: 209,889

[22] Filed: Jun. 13, 1988

[51] Int. Cl.$^5$ ............................................. A61B 17/42
[52] U.S. Cl. .................................... 604/356; 604/357; 606/119; 248/503; 182/138; 2/48
[58] Field of Search ............... 128/352, 361, 845, 846, 128/853; 604/356, 357; 224/157, 158; 5/503, 507, 512, 81 R, 82 R, 414, 424, 98 B, 95; 2/48, 51, DIG. 7, 49 A, 114; 297/182; 182/138, 139; 606/119

[56] References Cited

U.S. PATENT DOCUMENTS

| 519,713 | 5/1894 | Jackson | 604/357 |
|---|---|---|---|
| 756,544 | 4/1904 | Townsend | 604/357 |
| 1,454,112 | 12/1922 | Graves | 5/89 |
| 1,707,647 | 4/1929 | Still | 5/414 |
| 2,616,085 | 11/1952 | Bottolfsen | 2/49 A |
| 3,216,423 | 11/1963 | Blonsky et al. | 124/6 |
| 3,386,444 | 6/1986 | Brenner et al. | 604/357 |
| 3,494,356 | 2/1970 | Melges | 604/357 |
| 4,007,741 | 2/1977 | Waldrop | 128/846 |
| 4,149,537 | 4/1979 | Haswell | 604/357 |
| 4,170,991 | 10/1979 | Kella | 128/845 |
| 4,221,371 | 9/1980 | Kuphal | 604/356 |
| 4,301,544 | 11/1981 | Burton | 2/49 A |
| 4,742,587 | 5/1988 | Dove | 5/82 R |
| 4,817,836 | 4/1989 | Bates | 5/89 B |
| 4,823,418 | 4/1989 | Downs | 5/503 |
| 4,880,418 | 11/1989 | Tramont | 604/356 |

FOREIGN PATENT DOCUMENTS 0092784 2/1983 European Pat. Off. ............... 5/109

Primary Examiner—John D. Yasko
Assistant Examiner—Anthony Gutowski
Attorney, Agent, or Firm—Brady, O'Boyle & Gates

[57] ABSTRACT

A neo-natal safety net for selective connection between a delivery table and an attending obstetrician, or between a delivery table and a neo-natal table, thereby providing a safety net for the space therebetween for catching a newborn infant in the event that the baby accidentally slips from the hands of the obstetrician after delivery, or from the hands of an attending nurse during the post-natal care of the baby.

3 Claims, 1 Drawing Sheet

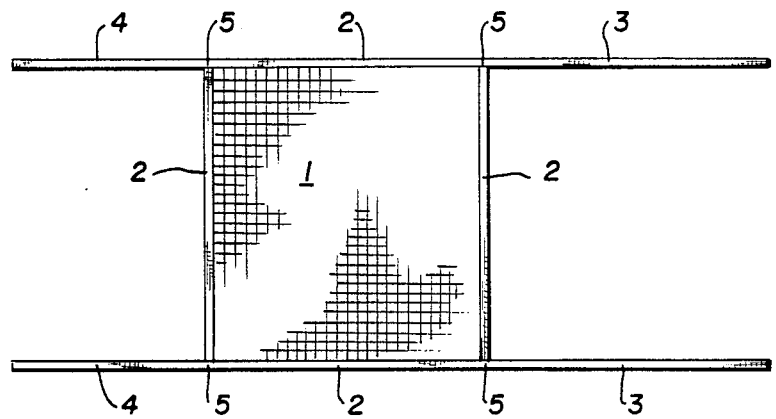
FIG.1
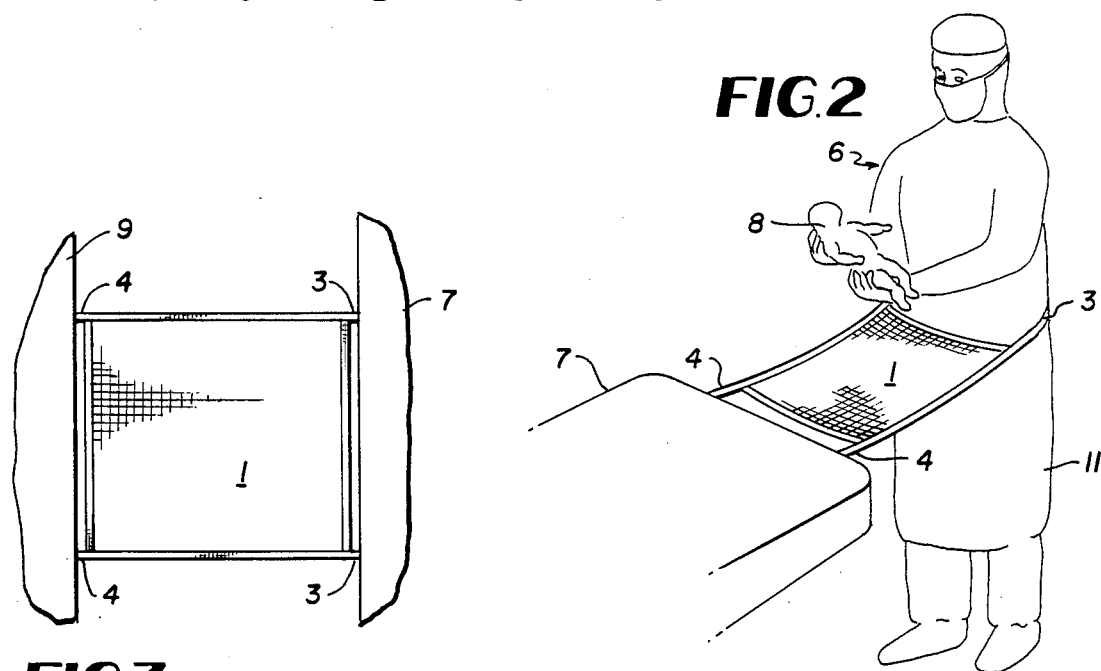
FIG.2
FIG.3
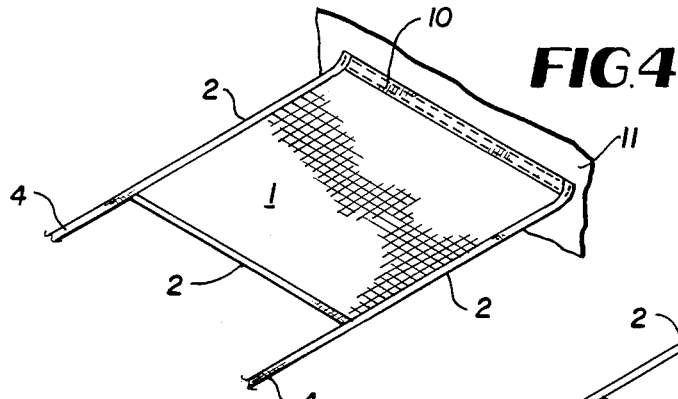
FIG.4
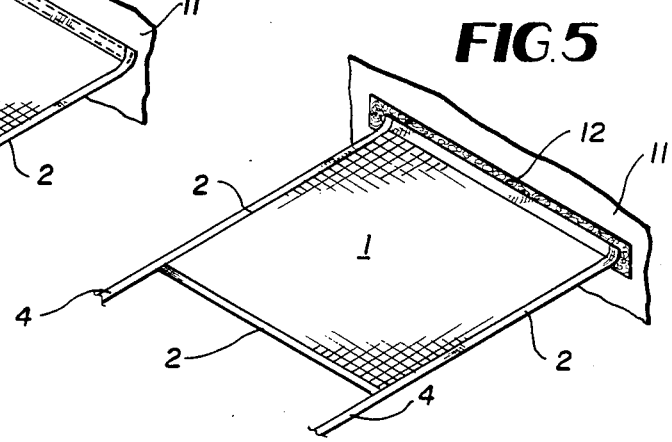
FIG.5

NEO-NATAL NET

BACKGROUND OF THE INVENTION

Hospitals are required to provide the utmost in medical care and safety to their patients, and most particularly to maternity patients during the birth and delivery of babies. While the attending obstetrician has been educated in the medical arts to be aware of the well-being of the expectant mother during the prenatal period through the safe delivery and birth of the baby, there is always a necessity to safely handle the baby immediately after delivery particularly due to the fact that the infant is covered with a fluid rendering the baby slippery; and thus not easily handled for subsequent post-natal care.

After considerable research and experimentation, the neo-natal device of the present invention has been devised to enhance the safety of the newborn child while being handled by the attending obstetrician immediately after delivery, or by attending nurses during the post-natal care of the baby.

The neo-natal device of the present invention comprises, essentially, a net having connecting members on each side thereof adapted for connecting the net between the delivery table and the attending obstetrician, whereby the net is suspended over the space between the delivery table and the obstetrician, to thereby provide a safety net for catching the newborn infant in the event that the baby accidentally slips from the hands of the obstetrician.

The neo-natal net can also be employed between the delivery table and the conventional neo-natal table to provide a safety net therebetween.

While, in one embodiment, the net is detachably connected to the waist of the attending obstetrician, in another embodiment the side of the net can be fixedly secured to the obstetrician's surgical gown as by stitching.

BRIEF DESCRIPTION OF THE DRAWING

FIG. 1 is a top plan view of the net:

FIG. 2 is a perspective view of the net extending between the delivery room table and the attending physician;

FIG. 3 is a top plan view of the net extending between the operating room table and the neo-natal table:

FIG. 4 is a perspective view of another embodiment wherein one end of the net is stitched to the physician's surgical gown; and FIG. 5 is a perspective view of still another embodiment wherein one end of the net is detachably connected to the surgical gown by means of Velcro.

DESCRIPTION OF THE PREFERRED EMBODIMENTS

Referring to the drawing and more particularly to FIG. 1, the neo-natal device of the present invention comprises a rectangular net 1 having selvedged edges 2, and connecting members 3 and 4 secured to the corners 5 of the net 1. In the embodiment shown in FIGS. 1 and 2, the connecting members 3 and 4 are in the form of straps adapted to encircle the waist of the attending obstetrician 6 and to be connected to the delivery table 7, respectively, whereby the net is suspended over the space between the obstetrician 6 and delivery table 7, to thereby provide a safety net for catching the newborn infant 8 in the event that the baby accidentally slips from the hands of the obstetrician.

While FIG. 2 shows the neo-natal net 1 extending between the delivery table 7 and the obstetrician 6, FIG. 3 illustrates the net 1 extending between the delivery table 7 and a conventional neo-natal table 9, to thereby provide a safety net therebetween.

In the embodiment shown in FIG. 2, the connecting members 3 are in the form of straps or ties encircling the waist of the obstetrician. As will be seen in FIGS. 4 and 5, the connecting members 3 can be omitted and the net can be either stitched as at 10 to the obstetrician's gown 11, or detachably connected thereto by means of Velcro 12.

It is to be understood that the forms of the invention herewith shown and described are to be taken as preferred examples of the same, and that various changes in the shape, size and arrangement of parts may be resorted to, without departing from the spirit of the invention or scope of the sub-joined claims.

We claim:

1. A neo-natal safety net connected between the end of a delivery table and the end of a neo-natal table spaced from said delivery table comprising, a net, a pair of straps secured to opposite sides of the net, the pair of straps on one side of the net connecting the net to the end of the delivery table, and the pair of straps on the other side of the net connecting the net to the end of the neo-natal table, whereby the net is suspended over the space between the delivery table and the neo-natal table in substantially a horizontal plane extending between the ends of the tables, to thereby provide a safety net for catching a newborn infant in the event that the baby accidentally slips from the hands while being handled during post-natal care.

2. A neo-natal safety net connected between a delivery table and the waist portion of a surgical gown adapted to be worn by an attending obstetrician comprising, a net, a pair of straps on one side of the net being connected to the delivery table, the opposite side of the net being stitched to the waist portion of the surgical gown, whereby the net is suspended over the space between the end of the delivery table and the waist of the obstetrician in substantially a horizontal plane extending between the end of the delivery table and the obstetrician's waist, to thereby provide a safety net for catching a newborn infant in the event that the baby accidentally slips from the hands of the obstetrician immediately after delivery.

3. A neo-natal safety net connected between a delivery table and the waist portion of a surgical gown adapted to be worn by an attending obstetrician comprising, a net, a pair of straps on one side of the net being connected to the delivery table, the opposite side of the net being connected to the waist portion of the surgical gown by a Velcro fastener, one connecting portion of the fastener extending along the edge of said opposite side of the net, the other connecting portion of the fastener being secured to and extending along the waist portion of the surgical gown, whereby the net is suspended over the space between the end of the delivery table and the waist of the obstetrician in substantially a horizontal plane extending between the end of the delivery table and the obstetrician's waist, the thereby provide a safety net for catching a newborn infant in the event that the baby accidentally slips from the hands of the obstetrician immediately after delivery.

* * * * *